United States Patent
Kaethner et al.

(10) Patent No.: US 11,969,222 B2
(45) Date of Patent: Apr. 30, 2024

(54) ACTUATING AN X-RAY DEVICE AND MEDICAL SYSTEM

(71) Applicant: Siemens Healthcare GmbH, Erlangen (DE)

(72) Inventors: Christian Kaethner, Forchheim (DE); Andreas Meyer, Bubenreuth (DE); Anton Nekovar, Neunkirchen (DE); Markus Kowarschik, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 291 days.

(21) Appl. No.: 17/500,936

(22) Filed: Oct. 13, 2021

(65) Prior Publication Data

US 2022/0117671 A1 Apr. 21, 2022

(30) Foreign Application Priority Data

Oct. 15, 2020 (DE) .................... 10 2020 213 035.3

(51) Int. Cl.
*A61B 6/06* (2006.01)
*A61B 6/00* (2006.01)
(Continued)

(52) U.S. Cl.
CPC ............... *A61B 34/20* (2016.02); *A61B 6/02* (2013.01); *A61B 6/06* (2013.01); *A61B 6/469* (2013.01);
(Continued)

(58) Field of Classification Search
None
See application file for complete search history.

(56) References Cited

U.S. PATENT DOCUMENTS 6,331,181 B1 * 12/2001 Tierney ................. A61B 34/37
606/130
8,828,021 B2 * 9/2014 Wenderow ........ A61M 25/0147
606/1
(Continued)

FOREIGN PATENT DOCUMENTS

DE    102020204454 A1 * 11/2020 ............... A61B 6/06
EP    3406291 B1   12/2019
WO    2020102665 A1  5/2020

OTHER PUBLICATIONS

German Office Action for German Application No. 10 2020 213 035.3 dated Jul. 2, 2021.

*Primary Examiner* — Thomas R Artman
(74) *Attorney, Agent, or Firm* — Lempia Summerfield Katz LLC

(57) ABSTRACT

A method for actuating an X-ray device during robot-assisted navigation of at least two objects introduced into a body, such as a hollow organ, of a patient by at least one robotic system, includes providing a first selection criterion for selecting one of the objects, and providing a second selection criterion for selecting one of the objects. One of the at least two objects is selected based on the first selection criterion and the second selection criterion, and recording parameters of the X-ray device are automatically set, such that the selected object in an X-ray image to be recorded is highlighted compared to the at least one other object. The selected object may be highlighted with respect to image quality, image flavor, positioning on the X-ray image, and/or a collimator setting of a collimator of the X-ray device. An X-ray image is recorded with the set recording parameters.

14 Claims, 5 Drawing Sheets

(51) Int. Cl.
  *A61B 6/02* (2006.01)
  *A61B 6/12* (2006.01)
  *A61B 6/46* (2024.01)
  *A61B 34/20* (2016.01)
  *A61B 34/30* (2016.01)
  *G06F 3/01* (2006.01)

(52) U.S. Cl.
  CPC ............ *A61B 6/487* (2013.01); *A61B 6/5211* (2013.01); *A61B 6/545* (2013.01); *A61B 6/548* (2013.01); *A61B 6/563* (2013.01); *A61B 34/30* (2016.02); *G06F 3/013* (2013.01); *A61B 2034/2065* (2016.02); *A61B 2034/301* (2016.02)

(56) References Cited

U.S. PATENT DOCUMENTS

| | | | |
|---|---|---|---|
| 9,931,087 B2* | 4/2018 | Melman | A61B 6/4233 |
| 10,268,915 B2* | 4/2019 | Wu | A61B 6/06 |
| 10,327,717 B2* | 6/2019 | Melman | A61B 6/4225 |
| 10,736,585 B2* | 8/2020 | Melman | A61B 6/5205 |
| 11,564,643 B2* | 1/2023 | Nekovar | A61B 6/12 |
| 2002/0032452 A1* | 3/2002 | Tierney | A61B 34/76 606/130 |
| 2005/0203384 A1* | 9/2005 | Sati | G06F 3/017 600/426 |
| 2007/0129626 A1* | 6/2007 | Mahesh | A61B 34/20 600/407 |
| 2010/0076308 A1 | 3/2010 | Wenderow et al. | |
| 2015/0313558 A1* | 11/2015 | Melman | A61B 6/5205 378/62 |
| 2016/0192892 A1* | 7/2016 | Guez | A61B 6/469 378/147 |
| 2018/0129896 A1* | 5/2018 | Wu | A61B 6/469 |
| 2019/0269374 A1* | 9/2019 | Melman | A61B 6/4225 |
| 2020/0121402 A1 | 4/2020 | Pedreira De Cerqueira Filho | |
| 2020/0359976 A1* | 11/2020 | Nekovar | G06T 7/246 |
| 2022/0117671 A1* | 4/2022 | Kaethner | A61B 34/20 |

* cited by examiner

ACTUATING AN X-RAY DEVICE AND MEDICAL SYSTEM

This application claims the benefit of German Patent Application Number DE 10 2020 213 035.3, filed on Oct. 15, 2020, which is hereby incorporated by reference in its entirety.

BACKGROUND

The present embodiments relate to actuating an X-ray device during robot-assisted navigation of at least two objects introduced into a body of a patient by at least one robotic system.

Interventional medical procedures in or via the vascular system of a body of a patient require medical objects (e.g., devices or instruments) to be introduced into the vascular system via a percutaneous vascular access and guided to the target region to be treated. As a development of manual navigation of the objects in the vascular system, a robotic system is connected between the hands of the practitioner and the patient, with the advantage that the practitioner no longer has to stand directly at the positioning table for the patient, but may maneuver the objects (e.g., rotation movement, forward movement, and backward movement) remotely. Such robotic systems by which robot-assisted automatic movement (e.g., semi-automatic movement) of an object (e.g., a catheter and/or guide wire) may be effected in a cavity organ of a patient, are known in principle, for example, from EP 3406291 B1. For this purpose, the practitioner is provided with a corresponding user interface for the remote-controlled movements.

The assistance is generally provided by an imaging device (e.g., an X-ray device) that allows the practitioner to monitor and follow the progress of the treatment (e.g., the position of the object) in real time using image data. For this purpose, it is, for example, possible for a series of two-dimensional fluoroscopic X-ray images to be created. In order to give the practitioner the best possible overall visual image flavor, the image data is recorded using suitable recording parameters. In the case of an X-ray device, the recording parameters may, for example, be formed by an X-ray voltage, an X-ray dose, an X-ray current, a diaphragm setting, a filter setting, a duration of an X-ray window, or an intensity. The selection of the recording parameters may take place either statically (e.g., single adaptation without further adaptive adaptations) or dynamically (e.g., repeated adaptive adaptations) and in this case generally affect the overall image flavor.

However, during an intervention, it may be important for an operator to obtain a specific adaptation of, for example, the image flavor or the section of the image (e.g., focused on a certain medical object). The operator may make an adaptation via an automatic general setting or a manual specific setting of the recording parameters. However, frequently, this is either not specific enough for the object of interest or is too time-consuming if a new manual adaptation is necessary for every small change.

An example of this is the setting of X-ray diaphragms. With regard to radiation hygiene, it is advantageous for the X-ray beam bundle from the X-ray tube to be limited as much as possible. It has proven to be advantageous to make this limitation of the X-ray beam semi-transparent by overlaying in the region of interest (ROI) not in the field of vision of the operator. Thus, the patient may only receive the full X-ray dose in the field of vision of the examiner. When using a plurality of objects, it is necessary, for example, for the decision as to where the ROI should be positioned to be made manually.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method for medical imaging that enables an operator to focus on a relevant region of interest, such as during an intervention in the presence of a plurality of objects introduced into the body of a patient, is provided. As another example, a medical system suitable for performing the method is provided.

The method according to the present embodiments for actuating an imaging device (e.g., an X-ray device) during robot-assisted navigation of at least two objects introduced into the body (e.g., into a hollow organ) of a patient by at least one robotic system includes the following acts: providing a first selection criterion for selecting one of the objects; providing a second selection criterion for selecting one of the objects; selecting one of the at least two objects based on the at least two selection criteria; automatically setting recording parameters of the imaging device (e.g., the X-ray device), such that the selected object in an image to be recorded (e.g., an X-ray image) is highlighted, for example, compared to the at least one other object (e.g., with respect to image quality, image flavor, positioning on the X-ray image, and/or a collimator setting of a collimator of the imaging device, such as the X-ray device), and recording an image (e.g., an X-ray image) with the recording parameters set in this way.

The method according to the present embodiments enables an operator to obtain automatic focusing on the currently relevant object during an intervention without time-consuming manual selection. In this way, for example, the image flavor or image section is optimized for the selected object, and the operator obtains all the important information and may concentrate on the intervention. This reduces the time required for the operator and the patient, and thus the X-ray dose delivered to the patient, and improves the diagnosis and the quality of any therapy.

The selection criteria used for this purpose may, for example, be obtained from previously or currently created measurements from different modalities.

According to one embodiment, the first selection criterion is formed based on an evaluation of at least one image (e.g., an X-ray image) recorded in advance or live with respect to a structure of interest, or based on an evaluation of an eye tracking system with respect to an object of interest. The image or images (e.g., X-ray image or images) created in advance may, for example, be created as part of a series of fluoroscopic X-ray images, but the image or images may also be at least one three-dimensional volume image. The X-ray image or images may then be analyzed with respect to a structure of interest (e.g., with respect to the position of the objects); in the case of a plurality of X-ray images, for example, a movement of one of the objects may be analyzed. A selection criterion is then created on this basis. If an eye tracking system is present, the measurement data created with this system may be evaluated (e.g., with respect to the frequency with which the objects are viewed by the eye tracker operator). On this basis, it is then also possible for a selection criterion to be created based, for example, on the most frequently viewed object. Eye tracking systems are generally known.

According to a further embodiment, the second selection criterion is formed based on information from the at least one robotic system as to which object is currently being actuated or moved. For example, the selection criterion may be selected based on which of the objects is currently being moved or was last moved.

According to a further embodiment, one of the selection criteria is weighted more than the other. This is, for example, useful in the context of an even number of selection criteria. The decisive selection criterion may be set in advance.

According to a further embodiment, a third selection criterion is provided, and the object is selected based on the three selection criteria. For example, the third selection criterion may be formed based on an evaluation of an eye tracker with respect to an object of interest or based on an evaluation of at least one previously recorded X-ray image with respect to a structure of interest. It is then possible to select the object that satisfies at least two of the three selection criteria. It is also possible for more than three selection criteria (e.g., a plurality of selection criteria) to be provided and used.

According to a further embodiment, the recording parameters are formed by an X-ray voltage and/or an X-ray dose or an X-ray current or a diaphragm setting and/or a filter setting and/or a duration of an X-ray window and/or an intensity and/or positioning with respect to the central beam. For example, a diaphragm setting of the diaphragms of a collimator may be set such that the selected object is located in the center of an X-ray image to be recorded (e.g., the region of interest) and is irradiated with the full X-ray dose set. For this purpose, the diaphragms of the collimator are actuated. Additionally or alternatively, the regions around the central object (e.g., also the second, non-selected object) may be irradiated with a lower X-ray dose using semi-transparent diaphragms.

According to a further embodiment, an updated selection of an object takes place continuously or at regular intervals using at least one of the selection criteria, and the recording parameters of the imaging device (e.g., the X-ray device) are set, such that the updated selected object in an X-ray image to be recorded is highlighted compared to the at least one other object (e.g., with respect to image quality, image flavor, positioning on the X-ray image, and/or a diaphragm setting or collimator setting of a collimator of the X-ray device), and a further recording of an X-ray image with the recording parameters set in this way is performed. In this way, changes during the intervention may be picked up promptly and incorporated in the method. It may thus be provided that the automatic focusing on the currently relevant object is maintained, even if a different object than before becomes relevant. Therefore, if, for example, the object is changed and the robotic system now actuates and moves the second object instead of the first object, the second object is now selected, and the recording parameters are set thereto as described above (e.g., ROI).

According to a further embodiment, the X-ray image or images recorded are postprocessed, where the object selected by the selection criteria in the course of the postprocessing is highlighted with respect to image flavor. Therefore, for example, postprocessing acts such as edge sharpness, noise correction, adaptation of the image contrast, etc. may be applied specifically to the selected object in order to optimize its depiction.

The present embodiments also include a medical system for performing the method according to the present embodiments. The medical system includes an X-ray device for recording X-ray images with an X-ray source, an X-ray detector, and a collimator, and a system controller for actuating the X-ray device. The medical system also includes at least one robotic system with at least one robot-assisted drive system. The at least one robot-assisted drive system is configured to move at least two medical objects in a cavity organ of a patient. The medical system includes an evaluation unit for evaluating previously recorded X-ray images with respect to a structure of interest, a communication link between the system controller and the at least one robotic system for transmitting information from the at least one robotic system as to which object is currently being actuated or moved, and a selection unit for selecting one of the at least two objects based on the selection criteria. In addition, the medical system may have an eye tracking system for tracking eye movements of an operator, and a communication link between the system controller and the eye tracking system for transmitting information with respect to an object of interest.

DETAILED DESCRIPTION

Figure 1:
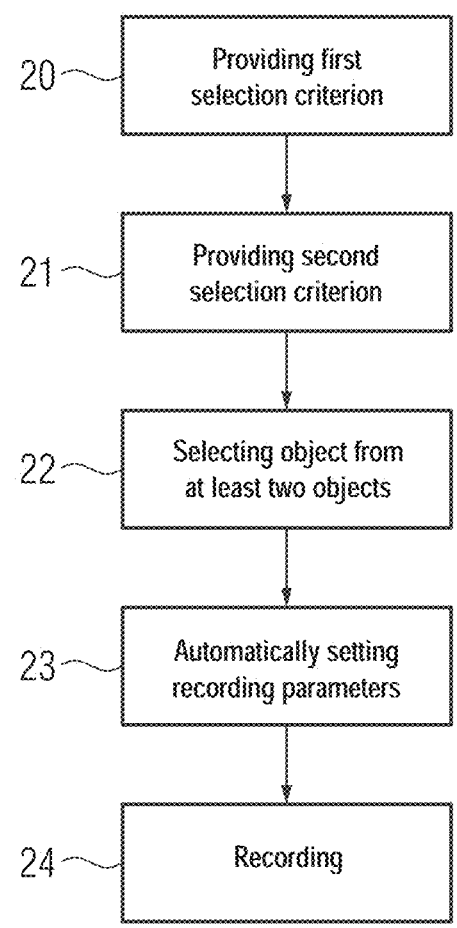
FIG. 1 shows a sequence of acts of one embodiment of a method.
Figure 2:
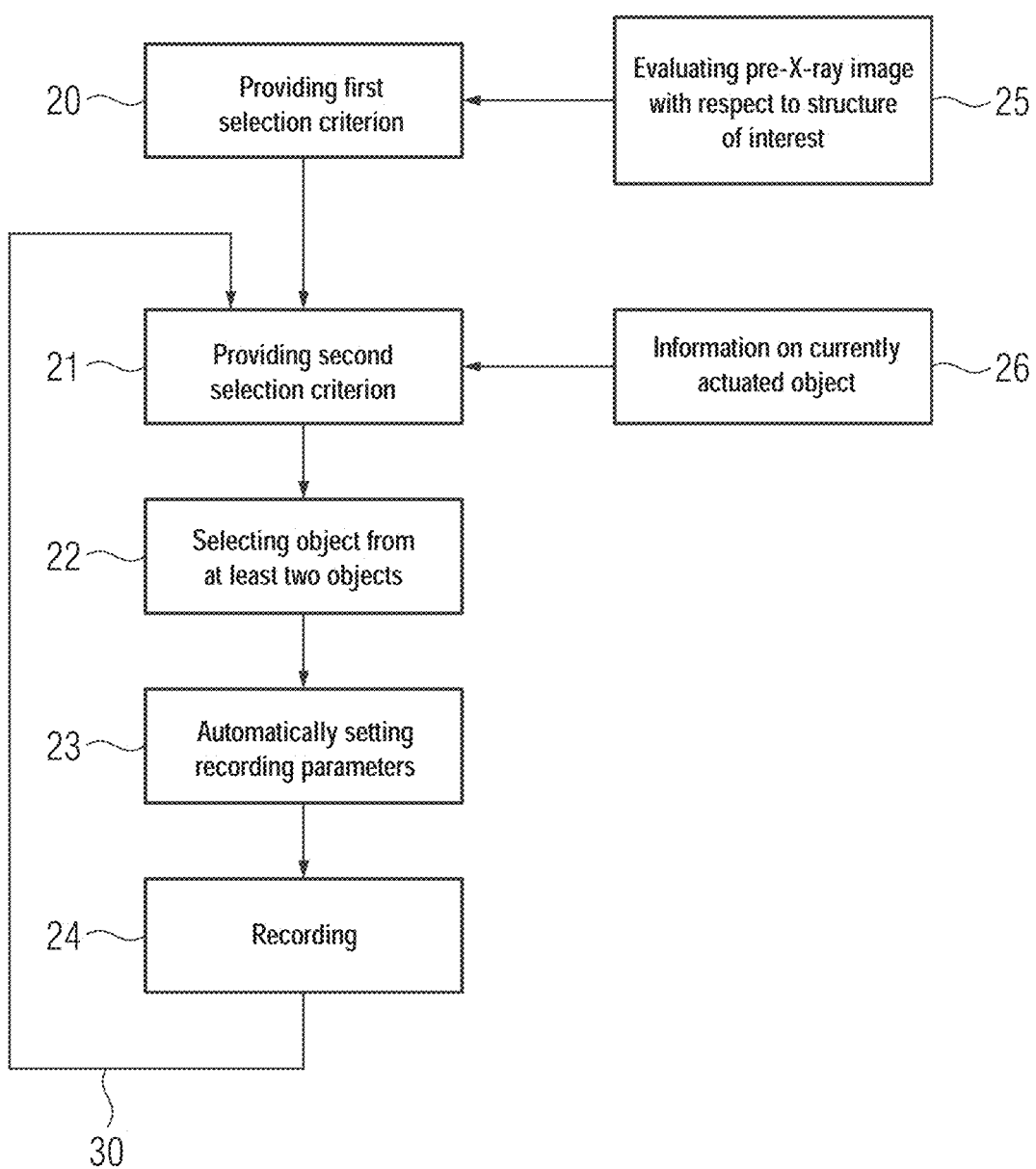
FIG. 2 shows a sequence of acts of a method according to FIG. 1 with further acts.

FIGS. 1 and 2 show acts of a method for actuating an X-ray device during robot-assisted navigation of at least two objects introduced into the body (e.g., into a hollow organ, such as a vascular system, vascular tree, bronchial system, etc.) of a patient by at least one robotic system. Robotic systems, by which robot-assisted automatic movement of an object in a hollow organ of a patient may be effected, are known in principle, for example, from EP 3406291 B1.

Figure 3:
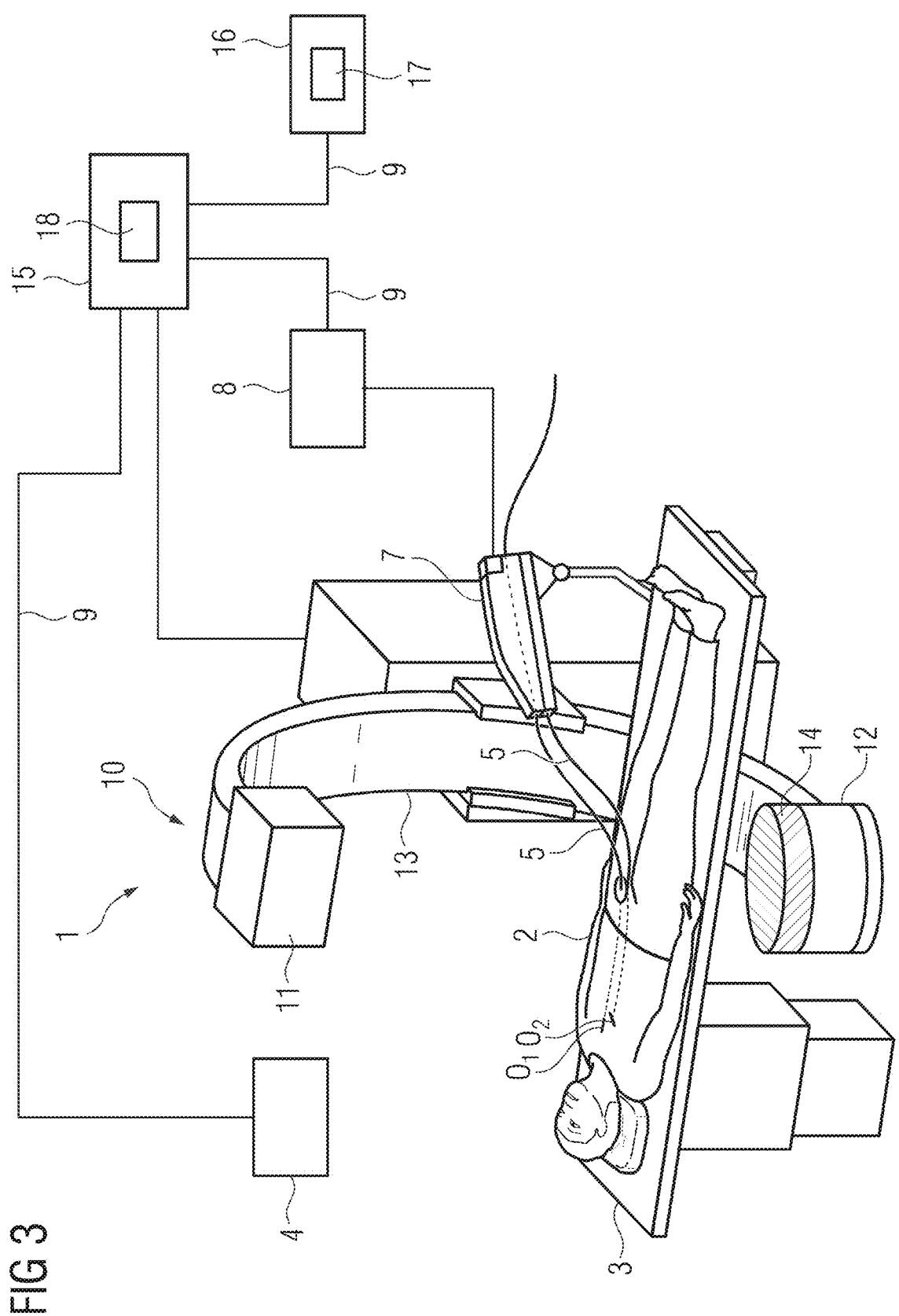
FIG. 3 is a view of one embodiment of a medical system.

FIG. 3 shows one embodiment of a medical system 1 for performing such a method. The medical system 1 has a robotic system and an X-ray device 10. The robotic system is configured for a semiautomatic or automatic movement of medical objects O1, O2 in a hollow organ of a patient 2. Herein, semiautomatic actuation may be, for example, actuation that may be transmitted to a robot controller 8 by an operator via an input unit (not shown; for example, joystick, touchpad, rotary regulator, etc.). In the example, it is initially assumed that there are two objects, a first object O1 and a second object P2. However, there may also be three or more objects. The objects may, for example, be catheters, stents, guide wires, or instruments. The objects O1, O2 are connected to the drive system 7 of the robotic system 7, 8 and may be navigated in a hollow organ of the patient 2 by the drive system 7. The movements are actuated by a robot controller 8. Alternatively, there may also be two drive systems or even two robotic systems for actuating the two objects.

The X-ray device 10 is provided to give an overview of the intervention and the movement. The X-ray device 10 has, for example, a C-arm 13 that holds an X-ray source 12 with a collimator 14 and an X-ray detector 11 and is connected to a system controller 15. The C-arm 13 is arranged to be movable relative to the patient 2; in the case of a mobile X-ray device, the entire X-ray device may also be moved. X-ray images of a mappable recording region may be created by the X-ray device 10, processed by an image system 16, and displayed on a display unit. The robot controller 8 and the system controller 15 of the X-ray device may exchange bidirectional data via a communication link 9 and communicate with one another.

The method according to the present embodiments is advantageous for obtaining a focusing on a specific medical object from a selection of at least two objects during an intervention with X-ray monitoring without constant manual effort.

In a first act 20 of the method for actuating the X-ray device, a first selection criterion for selecting one of the objects is provided. The first selection criterion may, for example, be an evaluation of at least one X-ray image or a series of X-ray images recorded previously or live (e.g., fluoroscopy images) with respect to a structure of interest (see the seventh act 25 in FIG. 2). The evaluation may, for example, be based on the calculation or estimation of probabilities. The X-ray image or images may be analyzed with respect to a structure of interest (e.g., with respect to the position of the objects); in the case of a series of X-ray images (e.g., fluoroscopy images), a movement of the objects (e.g., independent of breathing movements, movements of the heart, or other movements of a patient) may be analyzed. The evaluation may be performed by an evaluation unit 17. The information may be stored accordingly and made available for further analysis acts. An analysis may take place via conventional (e.g., model-based) approaches or also via a trained function (e.g., machine learning). The first selection criterion may then be provided on this basis.

Alternatively, if an eye tracking system 4 is present, for example, with a camera or camera glasses, the measurement data created with this system may be evaluated (e.g., with respect to the frequency with which the objects are viewed by the operator). On this basis, it is then also possible for a selection criterion to be provided that is, for example, based on which of the objects O1; O2 was viewed most frequently. The eye tracking system 4 has a communication link 9 with the system controller 15 by which data may be exchanged bidirectionally. All communication links 9 may be wireless or wired. Wireless communication links may, for example, function in the new 5G cellular standard using extremely low latency.

In a second act 21 of the method for actuating the X-ray device, a second selection criterion for selecting one of the objects is provided. For example, the second selection criterion is formed based on information from the at least one robotic system as to which object is currently being actuated or moved (see the eighth act 26 in FIG. 2). For example, the selection criterion may be selected based on which of the objects is currently being moved or was last moved. The information or data relating thereto may be exchanged and continuously updated via the communication link 9 between the robot controller 8 and the system controller 15.

Figure 5:
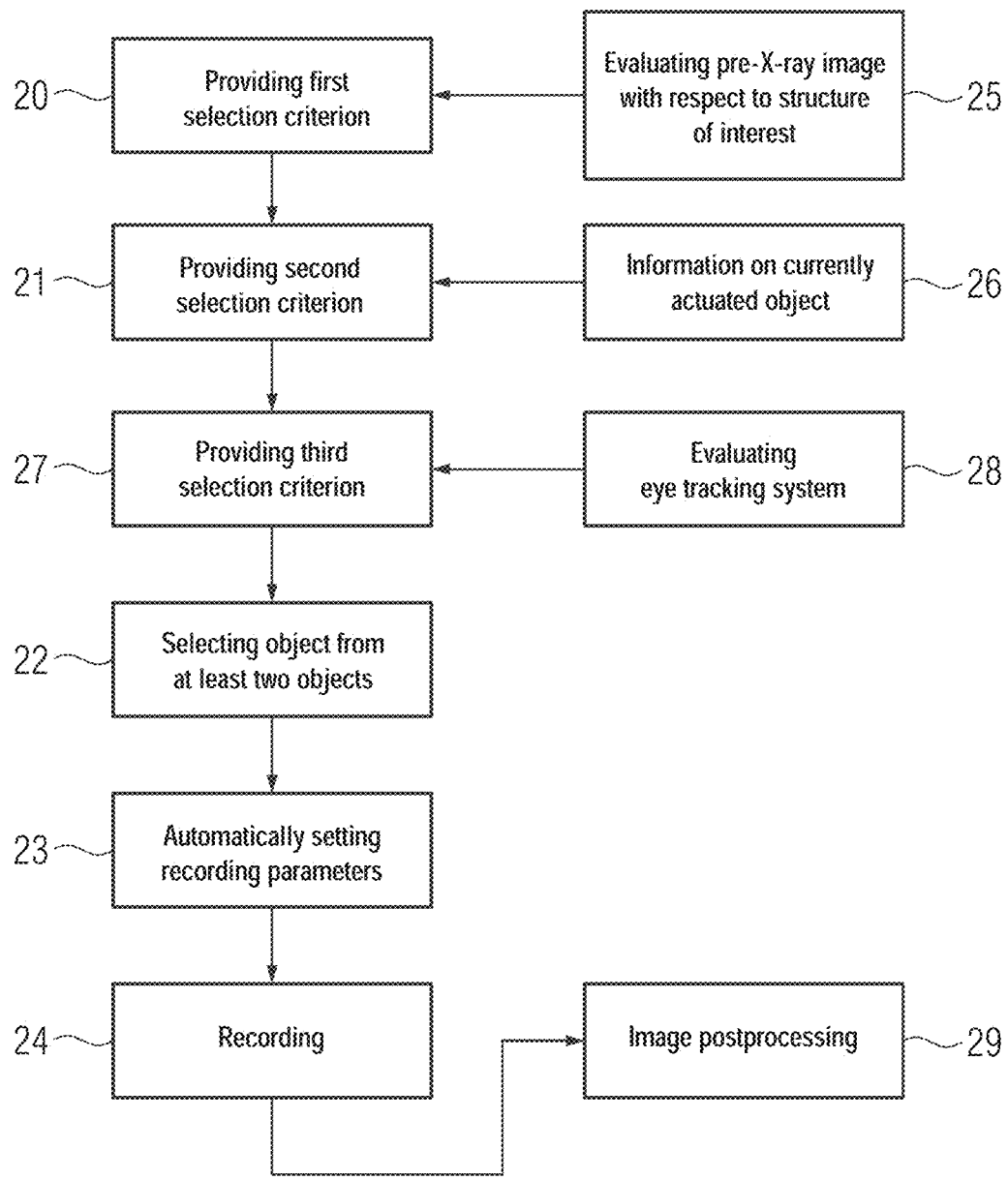
FIG. 5 shows a further sequence of acts of a method according to FIG. 1 with further acts.

As shown in FIG. 5, a third selection criterion may optionally also be provided in a third act 27. This may, for example, be based on which of the objects O1; O2 was viewed most frequently by an operator (see the ninth act 28 in FIG. 2), unless this is already formed by the first selection criterion. The information on the frequency with which the respective object is viewed is communicated to the system controller 15 via the eye tracking system 4.

The use of two or more selection criteria provides that an object is selected in a particularly well-informed manner, so that irregularities in the measurements have only a minor influence and disruptions to the intervention are minimized.

In a fourth act 22, one of the at least two objects is selected based on the two selection criteria. In this context, one of the selection criteria is weighted more than the other. This is, for example, useful in the case of an even number of selection criteria. It is possible to set, in advance, which of the selection criteria is weighted and how.

Figure 4:
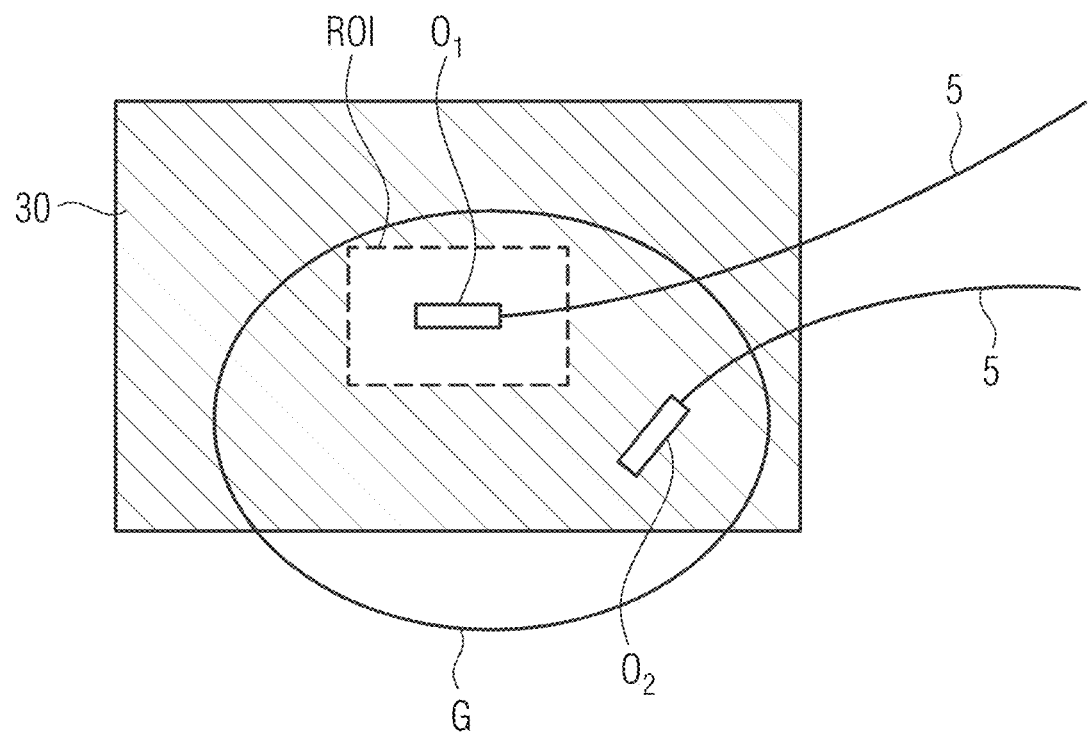
FIG. 4 is a view of an exemplary recording region with a region of interest.

In a fifth act 23, at least one recording parameter of the X-ray device is set automatically and, to be precise, such that the selected object in an X-ray image to be recorded is highlighted or optimized compared to the at least one other object and/or also compared to the remaining environment (e.g., with respect to image quality, image flavor, positioning on the X-ray image, and/or a collimator setting of a collimator of the X-ray device). The recording parameter or parameters may, for example, be an X-ray voltage, an X-ray dose, an X-ray current, a diaphragm setting, a filter setting, a duration of an X-ray window, or an intensity. Thus, the selected object (e.g., the first object O1) may be arranged centrally in the recording region 30 (e.g., in the region of interest (ROI); see FIG. 4). The region outside the region of interest ROI but within the recording region 30 in which, for example, the second object O2, which was not selected, is located, is overlaid semi-transparently by the diaphragms of the collimator 14. This reduces the time required by the operator and the patient and hence the X-ray dose delivered to the patient, and improves the diagnosis and the quality of any therapy. It is also or alternatively possible to use filters to attenuate the X-ray dose for the environment or to filter out radiation components. In one embodiment, the selected object may be overlaid non-centrally, and the remaining recording region may be overlaid semi-transparently by the diaphragms of the collimator 14. It may also be provided that the X-ray dose or the X-ray voltage or the X-ray current is optimized for the selected object. It may also be provided that the remaining recording region is recorded with lower resolution using binning.

In a sixth act 24, an X-ray image is then recorded with the set recording parameters. This results in an X-ray image that particularly highlights the selected object or optimizes the selected object with particularly good image quality or good image contrast. It is also possible for a series of X-ray images (e.g., fluoroscopy X-ray images) or one or more volume images to be created.

In a further embodiment, it is also, for example, possible for the method to be updated continuously or at regular intervals in a tenth act 30 (see FIG. 2). If a change has occurred (e.g., if another object is now moved by the robotic system or the robotic systems), an updated selection is made (fourth act 22) with at least one selection criterion (first act 20 and/or second act 21 and/or third act 27). Accordingly, the recording parameter or parameters are then automatically adapted to the currently selected object (fifth act 23), and at least one X-ray image is recorded (sixth act 24).

As shown in FIG. 5, after the recording of the at least one X-ray image, a postprocessing step 29 that further optimizes the selected object in the X-ray image using the selection may be performed. For example, adaptations with respect to the image contrast or the image noise or other types of image processing may be performed. It is also possible for highlighting to be provided by colors, frames, or different types of marking. In addition, an operator may also make further adaptations manually (e.g., markings or also types of image processing).

Various methods may also be used to support the automatic setting of recording parameters optimized for the selected object. Known methods for segmentation may be used. It is also possible to use information on the material composition of the objects in order, for example, to obtain and set the optimum X-ray dose or filtering. It is, for example, possible to use a previously prepared volume image (e.g., pre-op-image) or a depth estimation to ascertain the image plane in order to optimize the depth of field. In this context, it is also possible for a distance covered in the X-ray image (e.g., 2D X-ray image) to be calculated or estimated in order to be able to calculate the position of the object.

It may also be the case that a plurality of objects are moved at the same time (e.g., in the case of the presence of a first object, a second object and a third object, the second object and the third object are moved). In this case, either the respective other selection criterion (e.g., eye tracking system or image analysis) may be decisive; alternatively, the recording parameters may also be optimized for more than one object. Since the requirements for the adaptation of the depiction may then possibly not be unambiguous, it is possible that in such a case, a compromise solution, such as a kind of averaging, is performed with respect to the recording parameters.

It is also possible that an operator wishes to continue to highlight or to re-highlight an object at a later time (e.g., when another current object is already being viewed, such as in the course of the postprocessing). For this purpose, the necessary information may be stored accordingly and made available again later. Visualization may include either an adaptation of an existing previously recorded X-ray image, an overlaying of different X-ray images, or also a side-by-side depiction of a plurality of X-ray images. Further, it may be provided that the operator switches directly (e.g., even without a new viewing) between adapted X-ray images for the respective objects.

Further, in a further embodiment, it is also possible in all three variants to make subsequent local adaptations to image flavor (e.g., in order to highlight certain regions or structures or even to make the regions or structures less conspicuous in the depiction). This may take place via model-based functions or also trained functions.

The selection of the recording parameters and the image adaptations during the postprocessing may take place either statically (e.g., single adaptation without further adaptive adaptations) or dynamically (e.g., repeated adaptive adaptations) and in this case, generally affect the overall image flavor.

The present embodiments may be briefly summarized as follows: for a particularly simple and low-effort specific focusing on a certain medical object, a method is provided for actuating an X-ray device during robot-assisted navigation of at least two objects introduced into the body (e.g., into a hollow organ) of a patient by at least one robotic system, with the following acts: providing a first selection criterion for selecting one of the objects; providing a second selection criterion for selecting one of the objects; selecting one of the at least two objects based on the two selection criteria; automatically setting recording parameters of the X-ray device such that the selected object in an X-ray image to be recorded, for example, is highlighted compared to the at least one other object (e.g., with respect to image quality, image flavor, positioning on the X-ray image, and/or a collimator setting of a collimator of the X-ray device), and recording an X-ray image with the recording parameters set in this way.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for actuating an imaging device during robot-assisted navigation of at least two objects introduced into a body of a patient by at least one robotic system, the method comprising:
providing a first selection criterion for selecting an object of the at least two objects;
providing a second selection criterion for selecting the object or another object of the at least two objects;
selecting one object of the at least two objects based on at least the first selection criterion and the second selection criterion;
automatically setting recording parameters of the imaging device, such that the selected one object is highlighted in an image to be recorded; and
recording an image with the automatically set recording parameters.

2. The method of claim 1, wherein the imaging device is an X-ray device, and the body is a hollow organ.

3. The method of claim 1, wherein the recording parameters of the imaging device are automatically set, such that the selected one object is highlighted compared to the at least one other object of the at least two objects.

4. The method of claim 3, wherein the recording parameters of the imaging device are automatically set, such that the selected one object is highlighted compared to the at least one other object of the at least two objects with respect to image quality, image flavor, positioning on an X-ray image, a collimator setting of a collimator of the imaging device, or any combination thereof.

5. The method of claim 1, wherein one selection criterion of the first selection criterion and the second selection criterion is weighted more than the other selection criterion of the first selection criterion and the second selection criterion.

6. The method of claim 1, further comprising providing a third selection criterion,
wherein the one object is selected based also on the third selection criterion.

7. The method of claim 6, wherein the first selection criterion is formed based on an evaluation of at least one recorded image with respect to a structure of interest, or based on an evaluation of an eye tracking system with respect to an object of interest.

8. The method of claim 7, wherein the third selection criterion is formed based on an evaluation of an eye tracker with respect to an object of interest or based on an evaluation of at least one previously recorded X-ray image with respect to a structure of interest.

9. The method of claim 1, wherein the second selection criterion is formed based on information from the at least one robotic system as to which object is currently being actuated or moved.

10. The method of claim 1, wherein the recording parameters are formed by an X-ray voltage, an X-ray dose, an X-ray current, a diaphragm setting, a filter setting, a duration of an X-ray window, an intensity, positioning with respect to the central beam, or any combination thereof.

11. The method of claim 1, wherein an updated selection of the one object takes place continuously or at regular intervals using at least one selection criterion of the first selection criterion, the second selection criterion, and the third selection criterion, and the recording parameters of the imaging device are set such that the updated selected one object in an image to be recorded is highlighted compared to the at least one other object, and
wherein the method further comprises performing a further recording of an image with the set recording parameters set.

12. The method of claim 1, wherein the recorded image is postprocessed, and
wherein the one object selected based on the first selection criterion and the second selection criterion is highlighted with respect to image flavor in the course of the postprocessing.

13. A medical system for actuating an imaging device during robot-assisted navigation of at least two objects introduced into a body of a patient by at least one robotic system, the medical system comprising:
an X-ray device operable to record X-ray images, the X-ray device comprising an X-ray source, an X-ray detector, a collimator, and a system controller operable to actuate the X-ray device;
at least one robotic system comprising at least one robot-assisted drive system configured to move at least two medical objects in a cavity organ of a patient;
an evaluation unit configured to evaluate previously recorded X-ray images with respect to a structure of interest;
a communication link between the system controller and the at least one robotic system, the communication link configured to transmit information from the at least one robotic system as to which object of the at least two objects is currently being actuated or moved; and
a selection unit configured to select one of the at least two objects based on selection criteria.

14. The medical system of claim 13, further comprising:
an eye tracking system configured to track eye movements of an operator; and
a communication link between the system controller and the eye tracking system, the communication link being configured to transmit information with respect to an object of interest.

* * * * *